United States Patent [19]
Aggarwal et al.

[11] Patent Number: 5,703,246
[45] Date of Patent: Dec. 30, 1997

[54] PROCESS FOR THE PREPARATION OF AN OXIRANE, AZIRDINE OR CYCLOPROPANE

[75] Inventors: Varinder Kumar Aggarwal, Sheffield, United Kingdom; Hesham Nimer Hasan Abdel-Rahman, Nablus-Tubas, Israel; Hee Yoon Lee, Daejen, Rep. of Korea

[73] Assignee: Zeneca Limited, London, England

[21] Appl. No.: 617,755

[22] PCT Filed: Oct. 19, 1994

[86] PCT No.: PCT/GB94/02280

§ 371 Date: Mar. 15, 1996

§ 102(e) Date: Mar. 15, 1996

[87] PCT Pub. No.: WO95/11230

PCT Pub. Date: Apr. 27, 1995

[30] Foreign Application Priority Data

Oct. 22, 1993 [GB] United Kingdom ............ 9321803
Jun. 22, 1994 [GB] United Kingdom ............ 9412496

[51] Int. Cl.$^6$ .............................................. C07C 203/00
[52] U.S. Cl. ................... 548/955; 548/956; 548/968; 548/969; 549/215; 549/217; 549/519
[58] Field of Search ................... 548/955, 956, 548/968, 969; 549/215, 217, 519

[56] References Cited

PUBLICATIONS

Adams, J., et al. Tetrahedron, "Rhodium (II) Catalyzed Reactions of Diazocarbonyl Compounds", vol. 47 No. 10/11, 1991, pp. 1765–1808.
Aggarwal, V., et al., Phosphorus, Sulfur, and Silicon,"A Novel Catalytic Cycle for the Synthesis of Epoxides Using Sulfur Ylides, and Application to the Synthesis of Cyclopropanes and Azindines", 1994, vol. 95–96, pp. 283–292.
Doyle, M., Chem. Rev., "Catalytic Methods for Metal Carbene Transformations", 1986, vol. 86, pp. 919–939.
Furukawa, N. et al., J. Org. Chem., "Camphoryl Sulfide as a Chiral Auxiliary and a Mediator for One–Step Synthesis of Optically Active 1,2–Diaryloxiranes", 1989, vol. 54, pp. 4222–4224.
Hudlicky, T., et al., J. Org. Chem., "Terpenic Acids by Cyclopentane Annulation of Exocyclic Dienes. Synthesis of Triquinane Portion of Retigeranic Acid", vol. 47, pp. 1522–1527.
Jennings, W. et al., Tetrahedron, "The Titanium Tetrachloride Induced Synthesis of N–Phosphinoylimines and N–Sulphonylimines Directly from Aromatic Aldehydes", 1991, vol. 47, No. 29, pp. 5561–5568.
Jonczyk, A. et al., Synthetic Communications, "A Simple Method for Generation Diazo Compounds in an Aqueous Two–Phase System", 8(8), 1978, pp. 569–572.
Jonczyk, A., et al., Bull. Soc. Chim. Belg., "Reactions of Organic Anions. LXVII. Synthetic Utility Of Tosylhydrazones Reactions in Two–Phase Aqueous System", vol. 86, No. 9, 1977, pp. 739–740.
Chemistry & Industry, 15 Aug. 1994, p.642.
Derwent Abstracts, No. 33423A/19, 1978.

Primary Examiner—Johann Richter
Attorney, Agent, or Firm—Joseph R. Snyder

[57] ABSTRACT

A process for the preparation of an oxirane, aziridine or cyclopropane of formula (I) wherein, X is oxygen, NR$^4$ or CHR$^5$; R$^1$ is hydrogen, alkyl, aryl, heteroaromatic, heterocyclic or cycloalkyl; R$^2$ is hydrogen, alkyl, aryl, heteroaromatic, CO$_2$R$^8$, CHR$^{14}$NHR$^{13}$, heterocyclic or cycloalkyl; or R$^1$ and R$^2$ join together to form a cycloalkyl ring; R$^3$ is hydrogen, alkyl, aryl, heteroaromatic, CO$_2$R$^8$, R$^8{}_3$Sn, CONR$^8$R$^9$ or trimethylsilyl; R$^4$ and R$^5$ are, independently, alkyl, cycloalkyl, aryl, heteroaromatic, SO$_2$R$^8$, SO$_3$R$^8$, COR$^8$, CO$_2$R$^8$, CONR$^8$R$^9$ or CN, or R$^4$ can also be P(O)(aryl)$_2$; R$^8$ and R$^9$ are independently alkyl, aryl or arylalkyl; R$^{13}$ and R$^{14}$ are independently hydrogen, alkyl or aryl; the process comprising reacting a mixture of a compound of formula (II), wherein R$^1$, R$^2$ and X are as defined above, and a sulphide of formula SR$^6$R$^7$, wherein R$^6$ and R$^7$ are independently alkyl, aryl or heteroaomatic, or R$^6$ and R$^7$ join together to form a cycloalkyl ring which optionally includes an additional heteroatom, with either (i) a metallocarbon obtainable by reacting an alkylmetal with a methane derivative of formula CHR$^3$X'X", wherein R$^3$ is as defined above, and X' and X" are independently, a leaving group, or (ii) a metallocarbon obtainable by reacting a compound of formula (III), (wherein R$^3$ may not be hydrogen) with a suitable organometallic or inorganic reagent.

11 Claims, No Drawings

PROCESS FOR THE PREPARATION OF AN OXIRANE, AZIRIDINE OR CYCLOPROPANE

This application is a 371 of PCT/GB94/02280 filed Oct. 19, 1994.

The present invention relates to a process for the preparation of oxiranes from aldehydes or ketones, of aziridines from imines, or of cyclopropanes from alkenes.

It is known to generate ylides from diazo compounds in the presence of rhodium (II) acetate (M. P. Doyle et al J. Org. Chem. (1981) 46 5094–5102). The use of sulphur ylides to prepare oxiranes from carbonyl compounds is well known (see, for example, B. M. Trost and L. S. Melvin "Sulphur Ylides" Academic Press, 1975). Known methods require that the reaction is carried out under basic conditions. Thus, forming oxiranes of carbonyl substrates which also contain base sensitive groups is not straightforward. Also, known methods require stoichiometric amounts of sulphide and base.

According to the present invention there is provided a process for the preparation of an oxirane, aziridine or cyclopropane of formula (I), wherein, X is oxygen, $NR^4$ or $CHR^5$; $R^1$ is hydrogen, alkyl, aryl, heteroaromatic, heterocyclic, $NHR^{13}$ or cycloalkyl; $R^2$ is hydrogen, alkyl, aryl, heteroaromatic, $CO_2R^8$, $CHR^{14}NHR^{13}$, heterocyclic or cycloalkyl; or $R^1$ and $R^2$ join together to form a cycloalkyl ring; $R^3$ is hydrogen, alkyl, aryl, heteroaromatic, $CO_2R^8$, $R^8_3Sn$, $CONR^8R^9$ or trimethylsilyl; $R^4$ and $R^5$ are, independently, alkyl, cycloalkyl, aryl, heteroaromatic, $SO_2R^8$, $SO_3R^8$, $COR^8$, $CO_2R^8$, $CONR^8R^9$ or CN, or $R^4$ can also be $P(O)(aryl)_2$; $R^8$ and $R^9$ are independently alkyl, aryl or arylalkyl; $R^{13}$ and $R^{14}$ are independently hydrogen, alkyl or aryl; the process comprising reacting a mixture of a compound of formula (II), wherein $R^1$, $R^2$ and X are as defined above, and a sulphide of formula $SR^6R^7$ wherein $R^6$ and $R^7$ are independently alkyl, aryl or heteroaromatic, or $R^6$ and $R^7$ join together to form a cycloalkyl ring which optionally includes an additional heteroatom, with either (i) a metallocarbon obtainable by reacting an alkylmetal with a methane derivative of formula $CHR^3X'X''$, wherein $R^3$ is as defined above, and $X'$ and $X''$ are independently, a leaving group, or (ii) a metallocarbon obtainable by reacting a compound of formula (III) (wherein $R^3$ may not be hydrogen) with a suitable organometallic or inorganic reagent.

When the compound of formula (II) is an alkene (that is when X in the compound of formula (II) is $CHR^5$) it is an electron deficient alkene.

When a compound of formula (II) (wherein X is O and neither $R^1$ nor $R^2$ is hydrogen (ie it is a ketone)) is used in the process of the present invention to prepare a required oxirane of formula (I) (wherein X is O), the reactivity of the compound of formula (II) should be balanced against the nucleophilicity of the product obtained by reacting the metallocarbon of (i) or (ii) with a sulphide of formula $SR^6R^7$.

It is preferred that the process of the present invention is carried out in a solvent. Suitable solvents include chlorinated solvents (such as $CH_2Cl_2$ or $CHCl_3$), aromatic solvents (such as benzene, toluene and o-, m- or p-xylene), aliphatic alcohols (such as methanol, ethanol or tert-butanol), chain or cyclic ethers (such as diethyl ether, tert-butyl methyl ether, di-iso-propyl ether, glymes (for example monoglyme, diglyme or triglyme) or tetrahydrofuran), aliphatic or alicyclic hydrocarbons (such as n-hexane or cyclohexane), N,N-dimethylformamide, acetonitrile or N-methylpyrrolidone. The process may be carried out in a mixture of these solvents, or different reagents may be added in different solvents.

It is preferred that the process of the present invention is carried out at a temperature in the range −30°–100° C., especially in the range 0°–50° C., such as at ambient or room temperature.

The compounds of formula (I) have one, two or three chiral ring-carbon atoms and the process of the present invention is capable of forming all structural isomers of the compounds of formula (I). Chiral values of $R^1$, $R^2$, $R^3$, $R^4$ or $R^5$ can affect the stereochemical nature of the compound of formula (I) produced by the process of the present invention.

The term alkyl whenever it is used refers to straight or branched alkyl chains preferably containing from 1 to 10, especially from 1 to 6, for example from 1 to 4, carbon atoms. Alkyl is, for example, methyl, ethyl, n-propyl, n-butyl or tert-butyl.

Halogen is fluorine, chlorine, bromine or iodine.

Alkoxy and haloalkoxy groups are straight or branched chains, preferably containing from 1 to 4 carbon atoms.

Haloalkoxy and haloalkyl groups do not have a halogen that is susceptible to nucleophilic substitution. Thus, a carbon atom of a haloalkyl or haloalkoxy group must not carry a halogen atom and a hydrogen atom.

Aryl includes naphthyl but is preferably phenyl.

Heteroaromatic includes 5- and 6-membered aromatic rings containing one, two, three or four heteroatoms selected from the list comprising oxygen, sulphur and nitrogen and can be fused to benzenoid ring systems. Examples of heteroaromatic rings are pyridyl, pyrimidyl, pyridazinyl, pyrazinyl, triazinyl (1,2,3-, 1,2,4- and 1,3,5-), furyl, thienyl, pyrrolyl, pyrazolyl, imidazolyl, triazolyl (1,2,3- and 1,2,4-), tetrazolyl, oxazolyl, isoxazolyl, thiazolyl, isothiazolyl, quinolinyl, isoquinolinyl, cinnolinyl, quinazolinyl, quinoxalinyl, indolinyl, isoindolinyl, benzofuranyl, benzothienyl, benzimidazolyl, benzoxazole, benzthiazole, oxadiazole and thiadiazole.

Heterocyclic relates to non-aromatic rings and includes 5- and 6-membered rings containing one, two or three heteroatoms selected from the group comprising oxygen, sulphur and nitrogen. Examples are piperidine, pyrrolidine, azetidine, morpholine, tetrahydrofuran, tetrahydrothiophene, pyrroline, piperazine, isoxazoline and oxazoline. Heterocyclic rings are optionally substituted with one or more alkyl groups.

The ring formed when $R^6$ and $R^7$ join preferably contains from 1 to 12 (for example from 2 to 10, especially from 2 to 6) carbon atoms and optionally includes an additional heteroatom (preferably a nitrogen, oxygen or sulphur atom). The ring so formed can be substituted by one or more alkyl groups or can have one or two aryl rings fused to it (see, for example, (G)). Two ring carbons may be linked together through a carbon chain (optionally containing from 1 to 6 (preferably 1, 2, 3 or 4) carbon atoms) or through a chain comprising one or more oxygen and one or more carbon atoms (for example to form a methylenedioxy group). The further ring formed may be substituted by $C_{1-4}$ alkyl. The sulphide of formula $SR^6R^7$ is, for example, dimethylsulphide, diethylsulphide, (4-methoxyphenyl) methylsulphide or a sulphide of formula (A), (B), (C), (C'), (D), (E) or (F) wherein R' and R" are, independently, hydrogen, alkyl, aryl or arylalkyl.

Suitable organometallic or inorganic reagents preferably comprise rhodium or ruthenium. Suitable reagents include $Rh_2(OCOR^*)_4$, $Rh_2(NR^{15}COR^*)_4$ or $Ru_2(OCOR^*)_4$ (wherein $R^{15}$ is hydrogen, alkyl (especially methyl) or arylalkyl (such as benzyl; and R* is hydrogen, alkyl (preferably methyl), $C_{1-4}$ perfluoroalkyl (such as trifluoromethyl, 2,2,2-trifluoroethyl or pentafluoroethyl), aryl, (CHOH)alkyl or (CHOH)aryl), $Rh_2(OCOCH_3)_4$, $Rh_2(OCOCF_3)_4$, $Rh_2(NHCOCH_3)_4$, $Rh_2(NHCOCF_3)_4$, $RuCl_2(P(C_6H_5)_3)_2$, $RuCl(H_2C_2B_9H_{10})(P(C_6H_5)_3)_2$ or $Rh_6(CO)_{16}$. Alternatively, the rhodium or ruthenium reagent can comprise the group (H), wherein $R^{16}$ is alkyl, aryl or arylalkyl; and p is 2 or 3.

Alternatively, a suitable organometallic or inorganic reagent can comprise copper, nickel or palladium. Examples of suitable reagents include CuBr, CuCl, $CuOSO_2CF_3$, $CuBr_2$, $CuCl_2$, $CuSO_4$, $Cu(acetylacetate)_2$, $[Cu(CH_3CN)_4]BF_4$, $Pd(OCOCH_3)_2$, $Pd(CH_3CN)_2Cl_2$ or $Pd(C_6H_5CN)_2Cl_2$.

It is believed that a metallocarbene of formula $M=CHR^3$ (wherein M is, for example, rhodium, ruthenium, copper, nickel or palladium, and $R^3$ is as defined above but is not hydrogen) is produced by the reaction of a compound of formula (III) (wherein $R^3$ is not hydrogen) with a suitable organometallic or inorganic reagent.

A metallocarbon obtainable by reacting an alkylmetal (such as a dialkyl zinc or a trialkyl aluminium compound) with a methane derivative of formula $CHR^3X'X''$ (wherein $R^3$ is as defined above and X' and X'' are, independently, a leaving group) has a moiety that can be represented as M'—$CHR^3L$ (wherein M' is a metal, such as zinc or aluminium, $R^3$ is as defined above, and L is a leaving group). Such metallocarbons include zinc compounds which can be made, for example, by reacting a dialkyl zinc of formula $R^{11}R^{12}Zn$ [(wherein $R^{11}$ and $R^{12}$ are, independently, unsubstituted alkyl) and which is, for example, diethyl zinc], with a methane derivative of formula $CHR^3X'X''$ (wherein X' and X'' are, independently, a leaving group (such as a halogen (for example chlorine, bromine or iodine), a sulphurous acid (for example mesylate or tosylate), a carboxylate or a triflate) and which is, for example, $ClCHR^3I$ (such as $ClCH_2I$) or $R^3CHI_2$. These zinc compounds can be represented as X'—$ZnCHR^3X''$ (for example I—$ZnCH_2I$, I—$ZnCH_2Cl$ or I—Zn—$CHR^3I$) $Zn(CH_2X')_2$ or $R^{11}ZnCH_2X'$. Alternatively, such metallocarbons include aluminium compounds made, for example, by reacting a trialkyl aluminium of formula $R^{11}R^{12}R^{17}Al$ (wherein $R^{11}$, $R^{12}$ and $R^{17}$ are, independently, unsubstituted alkyl) with a methane derivative of formula $CHR^3X'X''$, wherein $R^3$, X' and X'' are as defined above. These aluminium compounds can be represented as $R^{11}R^{12}Al(CH_2X')$.

All alkyl groups can be substituted by one or more of aryl (such as phenyl), cycloalkyl (such as cyclopropyl), $C_{1-6}$ alkoxy (such as methoxy or ethoxy), $C_{1-6}$ thioalkyl (such as methylthio), halogen (to form, for example, $CF_3$ or $CH_2CF_3$), $C_{1-6}$ haloalkoxy (such as $OCF_3$) or $CO_2(C_{1-6})$ alkyl. In addition the alkyl groups of $R^4$ or $R^5$ may terminate with an aldehyde (C(H)=O) group or be interrupted with a carbonyl (C=O) group.

All aryl and heteroaromatic groups can be substituted. The groups, when substituted, are preferably substituted by one or more of alkyl, haloalkyl, $C_{1-6}$ alkoxy, halogen, $C_{1-6}$ haloalkoxy, cycloalkyl, nitro, cyano or $CO_2(C_{1-6})$alkyl.

Cycloalkyl rings contain, preferably from 3 to 7, especially from 3 to 6 carbon atoms. Cycloalkyl rings, can be substituted by one or more alkyl groups, $CO_2R^8$ (wherein $R^8$ is as defined above) or two ring carbons may be joined to each other by a carbon chain containing from 1 to 4 (preferably 1 or 2) carbon atoms to form a bicyclic structure.

In one aspect the present invention provides a process for the preparation of an oxirane, aziridine or cyclopropane of formula (I), wherein, X is oxygen, $NR^4$ or $CHR^5$; $R^1$ is hydrogen, alkyl, aryl, heteroaromatic, heterocyclic or cycloalkyl; $R^2$ is hydrogen, alkyl, aryl, heteroaromatic, $CO_2R^8$, heterocyclic or cycloalkyl; or $R^1$ and $R^2$ join together to form a cycloalkyl ring; $R^3$ is hydrogen, alkyl, aryl, heteroaromatic, $CO_2R^8$, $R^8{}_3Sn$ or trimethylsilyl; $R^4$ and $R^5$ are, independently, alkyl, cycloalkyl, aryl, heteroaromatic, $SO_2R^8$, $SO_3R^8$, $CO_2R^8$, $CONR^8R^9$; $R^8$ and $R^9$ are independently alkyl or aryl; the process comprising reacting a mixture of a compound of formula (II), wherein $R^1$, $R^2$ and X are as defined above, and a sulphide of formula $SR^6R^7$, wherein $R^6$ and $R^7$ are independently alkyl, aryl or heteroaromatic, or $R^6$ and $R^7$ join together to form a cycloalkyl ring which optionally includes an additional heteroatom, with either (i) a metallocarbon of formula M'—$CHR^3L$, wherein L is a leaving group and M' is a metal, or (ii) a metallocarbon obtainable by reacting a compound of formula (III) (wherein $R^3$ may not be hydrogen) with a suitable organometallic or inorganic reagent.

In another aspect the present invention provides a process for the preparation of an oxirane, aziridine or cyclopropane of formula (I), wherein, X is oxygen, $NR^4$ or $CHR^5$; $R^1$ is hydrogen, alkyl, aryl, heteroaromatic, heterocyclic, $NHR^{13}$ or cycloalkyl; $R^2$ is hydrogen, alkyl, aryl, heteroaromatic, $CO_2R^8$, $CHR^{14}NHR^{13}$, heterocyclic or cycloalkyl; or $R^1$ and $R^2$ join together to form a cycloalkyl ring; $R^3$ is hydrogen, alkyl, aryl, heteroaromatic, $CO_2R^8$, $R^8{}_3Sn$, $CONR^8R^9$ or trimethylsilyl; $R^4$ and $R^5$ are, independently, alkyl, cycloalkyl, aryl, heteroaromatic, $SO_2R^8$, $SO_3R^8$, $CO_2R^8$, $CONR^8R^9$ or CN; $R^8$ and $R^9$ are independently alkyl or aryl; $R^{13}$ and $R^{14}$ are independently hydrogen, alkyl or aryl; the process comprising reacting a mixture of a compound of formula (II), wherein $R^1$, $R^2$ and X are as defined above, and a sulphide of formula $SR^6R^7$, wherein $R^6$ and $R^7$ are independently alkyl, aryl or heteroaromatic, or $R^6$ and $R^7$ join together to form a cycloalkyl ring which optionally includes an additional heteroatom, with either (i) a metallocarbon of formula M'—$CHR^3L$, wherein L is a leaving group and M' is a metal, or (ii) a metallocarbon obtainable by reacting a compound of formula (III) (wherein $R^3$ may not be hydrogen) with a suitable organometallic or inorganic reagent.

In a further aspect the present invention provides a process as defined above wherein $R^1$ is hydrogen.

In a still further aspect the present invention provides a process comprising the steps:

a) reacting a metallocarbon (obtainable by reacting an alkyl metal with a methane derivative of formula $CHR^3X'X''$) with a sulphide of formula $SR^6R^7$; and b) reacting the product of (a) with a compound of formula (II).

In another aspect the present invention provides a process comprising the steps:

a) reacting an alkyl metal with a methane derivative of formula $CHR^3X'X''$;

b) reacting the product of (a) with a sulphide of formula $SR^6R^7$; and c) reacting the product of (b) with a compound of formula (II).

In a further aspect the present invention provides a process comprising the steps:

a) reacting a metallocarbon (obtainable by reacting a compound of formula (III) (wherein $R^3$ is not hydrogen) with a suitable organometallic or inorganic reagent) with a sulphide of formula $SR^6R^7$; and, b) reacting the product of (a) with a compound of formula (II).

In a still further aspect the present invention provides a process comprising the steps:

a) reacting a compound of formula (III) (wherein $R^3$ is not hydrogen) with a suitable organometallic or inorganic reagent;

b) reacting the product of (a) with a sulphide of formula $SR^6R^7$; and, c) reacting the product of (b) with a compound of formula (II).

In a further aspect the present invention provides a process for preparing a compound of formula (I) wherein the metallocarbon species is obtainable by reacting a compound of formula (III) (wherein $R^3$ is alkyl, aryl, heteroaromatic, $CO_2R^8$, $R^8{}_3Sn$, $CONR^8R^9$ or trimethylsilyl) with a suitable organometallic or inorganic reagent.

For the process (ii) it is preferred that the nucleophilicity of the sulphide of formula $SR^6R^7$ is such that the rate of reaction of the metallocarbon with the sulphide of formula $SR^6R^7$ is greater than the rate of reaction of the metallocarbon with the compound of formula (III).

In another aspect the present invention provides a process for preparing a compound of formula (I), wherein X, $R^1$, $R^2$, $R^3$, $R^4$ and $R^5$ are as defined above, the process comprising adding a compound of formula (III), wherein $R^3$ is as defined above, to a mixture of a sulphide of formula $SR^6R^7$, wherein $R^6$ and $R^7$ are as defined above, a compound of formula (II), wherein $R^1$, $R^2$ and X are as defined above, and an organometallic or inorganic reagent.

In a further aspect the present invention provides a process for preparing a compound of formula (I), wherein X, $R^1$, $R^2$, $R^3$, $R^4$ and $R^5$ are as defined above, the process comprising adding a mixture of a compound of formula (III), wherein $R^3$ is as defined above, and a sulphide of formula $SR^6R^7$, wherein $R^6$ and $R^7$ are as defined above, to a mixture of a compound of formula (II), wherein $R^1$, $R^2$ and X are as defined above, and an organometallic or inorganic reagent.

It is possible to influence the stereochemistry of the compound of formula (I) produced by the process. This can be done by using a chiral sulphide of formula $SR^6R^7$ (such as formulae (B) to (F)). The relative amounts of the stereochemical products will depend on the nature of the chiral sulphide used.

In another aspect the present invention provides the process (ii) as previously described wherein the organometallic reagent is present in a less than stoichiometric amount (such as from 0.5 to 0.001, for example from 0.015 to 0.005, equivalents).

In a further aspect the present invention provides the process (ii) as previously described wherein a solution of the compound of formula (III) (wherein $R^3$ is as defined above but is not hydrogen) is added slowly (for example over a period of 2–36, especially 5–24, hours) to a solution of a sulphide of formula $SR^6R^7$, a compound of formula (II) and an organometallic or inorganic reagent. By adding slowly a low concentration of the compound of formula (III) is maintained and the yield of the compound of formula (I) is increased. Under these conditions it is possible to use a less than a stoichiometric amount of sulphide (such as from 0.75 to 0.01, preferably from 0.75 to 0.1, for example from 0.5 to 0.1 (such as 0.2), equivalents).

In a still further aspect the present invention provides a process as hereinbefore described wherein the compound of formula (II) is an aldehyde, imine or alkene.

In another aspect the present invention provides a process as defined above wherein X is oxygen.

Where it is used, it is preferred that the compound of formula (III) is purified (for example by distillation) before being used in the process of the invention.

In a still further aspect the present invention provides a process for the preparation of a compound of formula (I) wherein X is as defined above (but is preferably oxygen) and $R^1$, $R^2$ and $R^3$ are as defined above (but $R^3$ is not hydrogen), the process comprising adding a compound of formula (III), wherein $R^3$ is as defined above (but not hydrogen), to a mixture of a compound of formula (II), wherein $R^1$ and $R^2$ are as defined above and X is oxygen, a sulphide of formula $SR^6R^7$, wherein $R^6$ and $R^7$ are as defined above, a compound of formula (II), wherein $R^1$ and $R^2$ are as defined above and X is oxygen, and a rhodium compound of formula $Rh_2(OCOR^*)_4$, wherein $R^*$ is as defined above (but is preferably methyl), the mixture being in the presence of a solvent. It is believed that this process proceeds as shown in Scheme 1.

In another aspect the present invention provides a process for the preparation of a compound of formula (I) wherein X is as defined above (preferably oxygen), and $R^1$, $R^2$ and $R^3$ are as defined above ($R^3$ is especially hydrogen) the process comprising adding a compound of formula $CHR^3X'X''$ to a compound of formula $R^{11}R^{12}Zn$ preferably in a suitable solvent preferably at a temperature in the range −50° to 10° C. (such as −30° to 0° C.) [to form a metallocarbon that can be represented as $Zn$—$CHR^3X'$], then adding a sulphide of formula $SR^6R^7$, and then adding a compound of formula (II) preferably at a temperature in the range 0° to 60° C. It is preferred that the compound of formula (II) is added some time after (for example 5–90, especially 10–60, minutes after) the sulphide of formula $SR^6R^7$ is added. It is believed that this process proceeds as shown in Scheme 2 It is preferred that this process is carried out under anhydrous conditions.

The following Examples illustrate the invention. The following abbreviations are used throughout the Examples:

m.p.=melting point
b.p.=boiling point
Ac=acetate
m=multiplet
s=singlet
d=doublet
dd=doublet of doublets
ddd=doublet of doublet of doublets
t=triplet
dt=doublet of triplets
ppm=parts per million
petrol=petroleum ether boiling in the range 60°–80° C.
Lit.[1]=C. G. Overberger et al J. Org. Chem. (1963) 28 592
Phenyl diazomethane can be prepared as described below or, alternatively, using the method described in Organic Synthesis 64 207. Where necessary, apparatus, reagents or solvents were dried before use.

EXAMPLE 1

N-Benzyl-p-toluene sulphonamide

To a solution of benzylamine (5 g, 4.67 mmol) in pyridine (25 ml) was added (cautiously) p-toluenesulphonyl chloride (10 g, 5.25 mmol). The deep red coloured solution was stirred at room temperature for 1 hour before being poured into water (80–100 ml). The oily precipitate which solidified on scratching was filtered and recrystallised from ethanol to give the title compound (10.98 g, 90% yield, m.p. 115°–116° C., (Lit.[1] 114° C.)). $\delta_H$ (CDCl$_3$): 7.80(2H,m); 7.25(7H,m); 4.95(1H,t); 4.05(2H,d); 2.35(3H,s)ppm.

N-Nitroso-N-benzyl-p-toluenesulphonamide

To a solution of N-benzyl-p-toluenesulphonamide (21 g, 80 mmol) and acetic acid (100 ml) in acetic anhydride (400 ml) was added solid sodium nitrite (120 g, 1.7 mol) in portions over a period of 12 hours at 5° C. The temperature was kept below 10° C. all the time. After the addition was finished the reaction mixture was stirred at room temperature for 18 hours. The reaction mixture was poured over an excess of ice water and stirred for 1 hour. The pale yellow precipitate was filtered and washed several times with water. The crude product was recrystallized from ethanol to give the title compound as a tiny yellow needles (19.1 g, 82% yield, m.p. 92°–93° C., (Lit.[1] 89°–90° C.). $\delta_H$ (CDCl$_3$): 7.80(2H,m); 7.25(7H,m); 4.95(2H,s); 2.40(3H,s)ppm.

Phenyldiazomethane (solution in tert-butyl methyl ether)

To a solution of sodium methoxide (1.2 equivalent, 4.0 ml of 1M solution in methanol) in tert-butyl methyl ether (12 ml) was added N-nitroso-N-benzyl-p-toluenesulphonamide (966 mg, 3.34 mmol) in small portions at room temperature. After the addition was finished the reaction mixture was refluxed for 15–30 minutes. The reaction mixture was cooled and washed with water (3×12 ml). The ethereal solution of phenyldiazomethane was dried over sodium sulphate for 30 minutes.

Decomposition of Phenyldiazomethane With Rh$_2$(OCOCH$_3$)$_4$ In the Presence of Dimethylsulphide and an Aldehyde The following general procedure was used for Examples 2–6. To a stirred solution of dimethylsulphide (0.5 mmol), rhodium (II) acetate (0.01 mmol) and the aldehyde (1 mmol) in dichloromethane (4 ml) was added a solution of phenyldiazomethane (2 mmol in 6 ml of tert-butyl methyl ether) at room temperature over a period of 24 hours. After the addition was completed the solvent was removed in vacuo and the residue was chromatographed over silica [eluent dichloromethane:petrol (2:3)].

EXAMPLE 2

Trans-Stilbene oxide

Following the procedure described in Example 1 and using benzaldehyde as the aldehyde, the title oxirane was obtained in 70% yield. $\delta_H$ (CDCl$_3$): 7.35(10H,m); 3.85(2H, s)ppm.

EXAMPLE 3

Trans-2-(4-Nitrophenyl)-3-phenyloxirane

Following the procedure described in Example 1 and using 4-nitrobenzaldehyde as the aldehyde, the title oxirane was obtained in 79% yield. $\delta_H$ (CDCl$_3$): 8.30(2H,m); 7.30 (7H,m); 3.95(1H,d); 3.85(1H,d)ppm.

EXAMPLE 4

2-Cyclohexyl-3-phenyloxirane

Following the procedure described in Example 1 and using cyclohexanecarboxaldehyde as the aldehyde, the title oxirane was obtained in 64% yield. The product was found to be a mixture of cis and trans (21:79) isomers. $\delta_H$ (CDCl$_3$): 7.20(5H,m); 4.10(1H,d) (cis isomer); 3.70(1H,d) (trans isomer); 2.85 (1H,d) (cis isomer); 2.75(1H,d) (trans isomer); 2.0–0.90 (11H,m)ppm. $\delta_C$ (CDCl$_3$): 138.18, 135.18(C), 128.42, 127.87, 127.91, 127.35, 126.33, 125.50, 67.43, 63.92, 57.46, 40.53, 34.92 (CH), 30.33, 29.62, 29.02, 28.10, 26.29, 25.20, 25.71, 25.56, 25.27, 25.20 (CH$_2$).

EXAMPLE 5

2-n-Butyl-3-phenyloxirane

Following the procedure described in Example 1 and using valeraldehyde as the aldehyde, the title oxirane was obtained in 59% yield. The product was found to be a mixture of cis and trans (44:56) isomers. $\delta_H$ (CDCl$_3$): 7.35(5H,m); 4.0(1H,d) (cis isomer); 3.55(1H,d) (trans isomer); 3.15(1H,d) (cis isomer); 2.85(1H,d) (trans isomer); 1.90–0.90(7H,m)ppm. $\delta_C$ (CDCl$_3$): 137.98, 135.82 (C), 128.58, 128.44, 127.98, 127.43, 126.49, 125.53, 63.12, 62.85, 59.57, 58.64, 57.46 (CH), 32.08, 28.18, 28.02, 22.55 (CH$_2$) 14.02, 13.89 (CH$_3$).

EXAMPLE 6

2-(1-Methylethyl)-3-phenyloxirane

Following the procedure described in Example 1 and using iso-butyraldehyde as the aldehyde, the title oxirane was obtained in 55% yield. The product was found to be a mixture of cis and trans (40:60) isomers. $\delta_H$ (CDCl$_3$): 7.35(5H,m); 4.05(1H,d) (cis isomer); 3.60(1H,d) (trans isomer); 2.85(1H,d) (cis isomer); 2.70(1H,d) (trans isomer); 1.64(1H,dd); 1.02(3H,d); 0.90(3H,d). $\delta_C$ (CDCl$_3$): 138.05, 135.85 (C), 128.43, 127.97, 127.38, 126.32, 125.52, 68.36, 65.18, 57.79, 57.65, 30.98, 25.87 (CH), 19.91, 19.04, 18.43, 17.91 (CH$_3$).

EXAMPLE 7

2-(4-Chlorophenyl)-3-phenyloxirane

To a stirred solution of a sulphide of formula (B), wherein R' is hydrogen, (0.5 mmol), rhodium (II) acetate (0.01 mmol) and 4-chlorobenzaldehyde (1 mmol) in dichloromethane (4 ml) was added a solution of phenyldiazomethane (1 mmol in 6 ml of tert-butylmethyl ether, as prepared in Example 1) at room temperature over a period of 24 hours. After addition was completed the solvent was removed in vacuo and the residue was chromatographed over silica (eluent dichloromethane:petrol, 2:3) to give the trans oxirane (160 mg, 70% yield and 11% ee) and the cis oxirane (30 mg, 16% yield).

EXAMPLE 8

Stilbene oxide

Following the procedure described in Example 7, but using benzaldehyde in place of p-chlorobenzaldehyde, trans stilbene oxide (117 mg, 61% yield and 11% ee) and cis stilbene oxide (23 mg, 10% yield) were obtained.

EXAMPLE 9

Trans-Stilbene oxide

To a stirred solution of tetrahydrothiophene (0.5 mmol), rhodium (II) acetate (0.01 mmol) and benzaldehyde (1 mmol) in dichloromethane (4 ml) was added a solution of phenyldiazomethane (1 mmol in 6 ml of tert-butylmethyl ether, as prepared in Example 1) at room temperature over a period of 24 hours. After addition was completed the solvent was removed in vacuo and the residue was chromatographed over silica (eluent dichloromethane:petrol, 2:3) to give the trans epoxide in 76% yield.

EXAMPLE 10

Trans-2-(4-Nitrophenyl)-3-phenyloxirane

Following the procedure described in Example 9, but using 4-nitrobenzaldehyde in place of benzaldehyde, the title oxirane was obtained in 78% yield.

EXAMPLE 11

2-(1-Methylethyl)-3-phenyloxirane

Following the procedure described in Example 9, but using iso-butyraldehyde in place of benzaldehyde, the title oxirane was obtained in 60% yield. The product was found to be a 55:45 mixture of trans:cis isomers.

EXAMPLE 12

2-Cyclohexyl-3-phenyloxirane

Following the procedure described in Example 9, but using cyclohexanecarboxaldehyde in place of benzaldehyde, the title oxirane was obtained in 72% yield. The product was found to be a 80:20 mixture of trans:cis isomers.

EXAMPLE 13

2-n-Butyl-3-phenyloxirane

Following the procedure described in Example 9, but using valeraldehyde in place of benzaldehyde, the title oxirane was obtained in 64% yield. The product was found to be a 52:48 mixture of trans:cis isomers.

EXAMPLE 14

Trans-2-Methyl-2-(4-nitrophenyl)-3-phenyloxirane

To a stirred solution of dimethylsulphide (73 µl, 1 mmol), rhodium (II) acetate (4.0 mg, 0.01 mmol) and p-nitroacetophenone (140 mg, 1 mmol) in dichloromethane (4 ml) was added a solution of phenyldiazomethane (1 mmol in 6 ml of tert-butylmethyl ether, as prepared in Example 1) at room temperature over a period of 24 hours. After addition was completed the solvent was removed in vacuo and the residue was chromatographed over silica (eluent dichloromethane:petrol, 2:3) to give the trans epoxide (143 mg, 56% yield) as a white solid m.p. 93°–94° C. $\delta_H$ (CDCl$_3$): 8.01(2H,m); 7.4(2H,m); 7.01(5H,m); 4.25(1H,s); 1.8(3H,s) ppm.

EXAMPLE 15

2-(Ethyl cycloprop-1-yl-2-carboxylate)-3-phenyloxirane

Using ethyl 2-formyl-1-cyclopropanecarboxylate, the title epoxide was obtained in 72% yield following the same procedure described in Example 9. The product was found to be a 50:50 mixture of cis:trans isomers on the epoxide ring. $\delta_H$ (CDCl$_3$): 7.25(5H,m); 3.75(1H,d); 3.6(1H,d); 2.95 (1H,dd); 2.8(1H,dd); 1.75(2H,m); 1.25(5H,m) ppm.

EXAMPLE 16

Phenyldiazomethane (solution in diethyl ether)

To a solution of sodium methoxide (600 µl of 1M solution in methanol) in diethyl ether (6 ml) was added N-nitroso-N-benzyl-p-toluenesulphonamide (483 mg, 1.67 mmol, prepared as in Example 1), in small portions at room temperature. After the addition was finished the reaction mixture was refluxed for 15–30 minutes. The reaction mixture was cooled and washed with water (3×6 ml). The etheral solution of phenyldiazomethane (1 mmol) was dried over sodium sulphate for 30 minutes.

Decomposition of Phenyldiazomethane With Rh$_2$(OCOCH$_3$)$_4$ In the Presence of Dimethylsulphide and an Aldehyde The following general procedure was used for Examples 17–21. To a stirred solution of dimethylsulphide (1 mmol), rhodium (II) acetate (0.01 mmol) and the aldehyde (1 mmol) in dichloromethane (4 ml) was added a solution of phenyldiazomethane (1 mmol in 6 ml of diethyl ether) at room temperature over a period of 3 hours. After the addition was completed the solvent was removed in vacuo and the residue was chromatographed over silica [eluent dichloromethane:petrol (2:3)].

EXAMPLE 17

Trans-Stilbene oxide

Following the procedure described in Example 16 and using benzaldehyde as the aldehyde, the title oxirane was obtained in 70% yield.

EXAMPLE 18

Trans-2-(4-Nitrophenyl)-3-phenyloxirane

Following the procedure described in Example 16 and using 4-nitrobenzaldehyde as the aldehyde, the title oxirane was obtained in 62% yield.

EXAMPLE 19

2-Cyclohexyl-3-phenyloxirane

Following the procedure described in Example 16 and using cyclohexanecarboxaldehyde as the aldehyde, the title oxirane was obtained in 66% yield. The product was found to be a mixture of cis and trans (21:79) isomers.

EXAMPLE 20

2-n-Butyl-3-phenyloxirane

Following the procedure described in Example 16 and using valeraldehyde as the aldehyde, the title oxirane was obtained in 55% yield. The product was found to be a mixture of cis and trans (44:56) isomers.

EXAMPLE 21

2-(1-Methylethyl)-3-phenyloxirane

Following the procedure described in Example 16 and using iso-butyraldehyde as the aldehyde, the title oxirane was obtained in 64% yield. The product was found to be a mixture of cis and trans (40:60) isomers.

EXAMPLE 22

Ethyl (3-phenyloxiran-2-yl)cycloprop-2-yl) carboxylate

Following the procedure described in Example 9, but using ethyl 2-formyl-1-cyclopropanecarboxylate in place of benzaldehyde, the title oxirane was obtained in 72% yield. The product was found to be a 50:50 mixture of trans:cis isomers. $\delta_H$ (CDCl$_3$): 7.25(5H,m); 3.75(1H,d,J=2 Hz) (cis isomer); 3.6(1H,d,J=2 Hz)(trans isomer); 2.95(1H,dd,J=2 Hz,J=3.5 Hz) (cis isomer); 2.8(1H,dd,J=2.0 Hz,J=4.5 Hz) (trans isomer); 1.75 (m,2H); 1.25(5H,m)ppm.

EXAMPLE 23

2-(4-Acetyloxyphenyl)-3-phenyloxirane

Following the procedure described in Example 9, but using 4-acetoxybenzaldehyde in place of benzaldehyde, the title oxirane was obtained in 20% yield. $\delta_H$ (CDCl$_3$): 7.10–7.45(9H,m); 3.85(1H,d,J=2 Hz); 2.80(1H,d,J=2.0 Hz); 2.25(3H,s)ppm.

EXAMPLE 24

Styrene oxide

To a solution of diethyl zinc (1.8 ml of 1.1M solution in toluene, 2.0 mmol) in 1,2-dichloroethane (6 ml) was added chloroiododomethane (218 μl, 3 mmol) at −15° C. and the reaction mixture was stirred for 15 minutes. Tetrahydrothiophene (240 μl, 3 mmol) and benzaldehyde (1 mmol) were added and the reaction mixture was warmed to room temperature. After stirring at that temperature for 1 hour the reaction mixture was refluxed for one hour. After cooling to room temperature, the reaction mixture was diluted with dichloromethane (20 ml) and washed with saturated solution of $NH_4Cl$ (3×5 ml). The organic layer was dried over $MgSO_4$. After filtration of the drying agent the solvent was removed in vacuo and the residue was chromatographed over silica (eluant petrol:dichloromethane (40:60) to give the title compound as a clear oil (92%).

EXAMPLE 25 p-Nitrostyrene oxide

Following the procedure described in Example 24, but using p-nitrobenzaldehyde, in place of benzaldehyde, the title oxirane was produced in 95% yield.

EXAMPLE 26

4-Chlorostyrene oxide

Following the procedure described in Example 24, but using 4-chlorobenzaldehyde in place of benzaldehyde, the title oxirane was produced in 65% yield.

EXAMPLE 27

Cyclohexylethylene oxide

Following the procedure described in Example 24, but using cyclohexane carboxaldehyde in place of benzaldehyde, the title oxirane was produced in 60% yield.

EXAMPLE 28

2-(4-Chlorophenyl)-3-phenyloxirane

To a stirred solution of tetrahydrothiophene (0.1 mmol), rhodium (II) acetate (0.01 mmol) and p-chlorobenzaldehyde (1 mmol) in dichloromethane (4 ml) was added a solution of phenyldiazomethane (1 mmol in 6 ml of tert-butylmethyl ether) at room temperature over a period of 24 hours. After addition was completed the solvent was removed in vacuo and the residue was chromatographed over silica to provide the title oxirane in 26% yield.

EXAMPLE 29

2-(4-Chlorophenyl)-3-phenyloxirane

To a stirred solution of dimethyl sulphide (0.1 mmol), rhodium (II) acetate (0.01 mmol) and p-chlorobenzaldehyde (1 mmol) in dichloromethane (4 ml) was added a solution of phenyldiazomethane (1 mmol in 6 ml of tert-butylmethyl ether) at room temperature over a period of 24 hours. After addition was completed the solvent was removed in vacuo and the residue was chromatographed over silica to provide the title oxirane in 46% yield.

EXAMPLE 30

2-(4-Chlorophenyl)-3-phenyloxirane

To a stirred solution of dimethyl sulphide (0.25 mmol), rhodium (II) acetate (0.01 mmol) and p-chlorobenzaldehyde (1 mmol) in dichloromethane (4 ml) was added a solution of phenyldiazomethane (1 mmol in 6 ml of tert-butylmethyl ether) at room temperature over a period of 24 hours. After addition was completed the solvent was removed in vacuo and the residue was chromatographed over silica to provide the title oxirane in 76% yield.

EXAMPLE 31

2-(4-Chlorophenyl)-3-phenyloxirane

To a stirred solution of dimethyl sulphide (0.20 mmol), rhodium (II) acetate (0.01 mmol) and p-chlorobenzaldehyde (1 mmol) in dichloromethane (4 ml) was added a solution of phenyldiazomethane (1 mmol in 6 ml of tert-butylmethyl ether) at room temperature over a period of 24 hours. After addition was completed the solvent was removed in vacuo and the residue was chromatographed over silica to provide the title oxirane in 76% yield.

EXAMPLE 32

Stilbene oxide

Following the procedure described in Example 31, but using benzaldehyde in place of p-chlorobenzaldehyde, the title oxirane was produced in 74% yield.

EXAMPLE 33

2-Cyclohexyl-3-phenyloxirane

Following the procedure described in Example 31, but using cyclohexane carboxaldehyde in place of p-chlorobenzeldehyde, the title oxirane was produced in 51% yield.

EXAMPLE 34

2-n-Butyl-3-phenyloxirane

Following the procedure described in Example 31, but using valeraldehyde in place of p-chlorobenzeldehyde, the title oxirane was produced in 45% yield.

EXAMPLE 35

2-(4-Nitrophenyl)-3-phenyloxirane

Following the procedure described in Example 31, but using p-nitrobenzaldehyde in place of p-chlorobenzeldehyde, the title oxirane was produced in 89% yield.

EXAMPLE 36

Phenyl diazomethane

N-Nitroso-N-benzyl-p-toluene sulphonamide (966 mg, 3.33 mmol) was added in small portions to a solution of sodium methoxide (2.0 ml of 2M solution in methanol) in t-butyl methyl ether (12 ml) and methanol (2 ml) at room temperature. After the addition was finished the reaction mixture was refluxed for 15–30 min. The reaction mixture was cooled and washed with water (3×6 ml). The ethereal solution of phenyl diazomethane was dried over sodium sulphate for 30 minutes. The solvent was removed in vacuo and the residue distilled under reduce pressure to give phenyl diazomethane as a dark red oil (30% yield, b.p. 20° C. at 1 mmHg) which was immediately dissolved in t-butyl methyl ether (6 ml).

General Method For Epoxidation Using Phenyldiazomethane, an Aldehyde and $Rh_2(OAc)_4$ in the Presence of Dimethyl Sulfide Phenyl diazomethane (1 mmol in 6 ml of t-butyl methyl ether) was added to a stirred solution of dimethyl sulfide (0.2 mmol), rhodium (II) acetate (4.0 mg, 0.01 mmol) and an aldehyde (1 mmol) in dichloromethane (4 ml) at room temperature over a period of 24 hours. After the addition was complete the solvent was removed in vacuo and the residue was chromatographed using silica [eluent dichloromethane:petrol (2:3)].

EXAMPLE 37

Stilbene oxide

Using the method of Example 36 with benzaldehyde gave the title compound in 74% yield as a mixture of cis and trans (12:88) isomers.

EXAMPLE 38

Trans-2-(4-Nitrophenyl)-3-phenyloxirane

Using the method of Example 36 with 4-nitrobenzaldehyde gave the title compound in 89% yield as a yellow solid m.p. 126°–128° C.

EXAMPLE 39

2-(4-Chlorophenyl)-3-phenyloxirane

Using the method of Example 36 with 4-chlorobenzaldehyde gave the title compound in 76% yield as a white solid and as a mixture of cis and trans (20:80) isomers.

EXAMPLE 40

2-Cyclohexyl-3-phenyloxirane

Using the method of Example 36 with cyclohexane carboxaldehyde gave the title compound in 51% yield as a clear oil and as a mixture of cis and trans (21:79) isomers.

EXAMPLE 41

2-n-Butyl-3-phenyloxirane

Using the method of Example 36 with valeraldehyde gave the title compound in 45% yield as a clear oil and as a mixture of cis and trans (44:56) isomers.

EXAMPLE 42

2,2-Dimethyl-4-(3-phenyloxiran-2-yl)-1,3-dihydrodioxole

Using the method of Example 36 with 2,2-dimethyl-4-formyl-1,3-dihydrodioxole but using 1 mmol of dimethyl sulfide gave the title compound in 73% yield as a clear oil and as a mixture of diastereomers. $\delta_H$ (CDCl$_3$, 400 MHz): 7.4–7.2(5H,m), 4.3–3.90(4.4H,m), 3.87(0.33H,d,J=2.0 Hz 3.83(0.34H,d,J=2.0 Hz), 3.62–3.56(0.33H, ddd,J=9.0 Hz,J= 6.0 Hz,J=5.0 Hz), 3.30(0.33H,dd, J=4.0 Hz, J=9.0 Hz), 3.15–3.10(0.67H,two dd, J=2.0 Hz, J=6.0 Hz), 1.30 and 1.25 (6H,s) ppm.

EXAMPLE 43

Ethyl 2,3-epoxy-3-phenyl propionate

Using the method of Example 36 with ethyl glyoxylate but using 1 mmol of dimethyl sulfide gave the title compound in 53% yield as a clear oil. $\delta_H$(CDCl$_3$, 250 MHz): 7.4–7.2(5H,m), 4.36–4.20 (2H,m), 4.10 (1H,d,J=2.0 Hz), 3.51 (1H,d,J=2.0 Hz), 1.50(3H,t,J=8 Hz)ppm.

EXAMPLE 44

1,3-Diphenyl-2,3-epoxypropane

Using the method of Example 36 with phenylacetaldehyde but using (1 mmol) of dimethyl sulfide gave the title compound in 80% yield as a clear oil. $\delta_H$ (CDCl$_3$, 250 MHz): 7.3–7.1 (10H,m), 3.55 (1H,d,J=2.0 Hz), 3.05 (1H, dt,J=6.0 Hz,J=2.0 Hz), 2.80 (2H,d,J=6.0 Hz)ppm.

EXAMPLE 45

Stilbene oxide

Phenyl diazomethane (1 mmol in 6 ml of t-butylmethylether) was added to a stirred solution of a sulphide of formula (B) wherein R' is hydrogen (0.2 mmol), rhodium (II) acetate (4.0 mg, 0.01 mmol) and benzaldehyde (1 mmol) in dichloromethane (4 ml) at room temperature over a period of 24 hours. After the addition was complete the solvent was removed in vacuo and the residue was chromatographed over silica [eluent dichloromethane:petrol (2:3)] to give the titled compound in 58% yield and 11% ee.

EXAMPLE 46

2-(4-Chlorophenyl)-3-phenyloxirane

Using the method of Example 45 with 4-chlorobenzaldehyde in place of benzaldehyde gave the title compound in 62% yield and 12% ee as a white solid. This was a mixture of cis and trans (16:84) isomers.

EXAMPLE 47

1-Benzoyl-2,3-diphenylcyclopropane

Phenyl diazomethane (prepared as in Example 36, 0.5 mmol in 3 ml of t-butyl methyl ether) was added to a stirred solution of dimethylsulphide (7.3 ml; 0.1 mmol), rhodium (II) acetate (2 mg; 0.005 mmol) and chalcone (103 mg; 0.5 mmol) in dichloromethane (2 ml) at room temperature over a period of 24 hours. After the addition was complete the solvent was removed in vacuo and the residue was chromatographed over silica [eluent dichloromethane:petrol (2:3)], to give the title compound as a 4:1 mixture of trans:cis cyclopropanes as a yellowy solid (58 mg; 39%).

$\delta_H$ (CDCl$_3$, 250 MHz); 3.27(0.8H,dd,J=6.5 and 9 Hz), 3.32(0.4H,d,J=5 Hz), 3.38(0.8H,dd,J=5.5 and 9.5 Hz), 3.54 (0.2H,t,J=5 Hz), 3.62(0.8H,dd,J=5.5 and 6.5 Hz), 7–7.5 (13H,m), 7.95(1.6H,m), 8.15(0.4H,m)ppm.

The same method was applied for the cyclopropanation of chalcone using a stoichiometric amount of dimethyl sulphide (36.5 µl; 0.5 mmol). Column chromatography over silica afforded the title compound as a 5:1 mixture of trans; cis cyclopropanes as a yellowy solid (54 mg; 36.2%.

EXAMPLE 48

Stilbene oxide

A solution of phenyldiazomethane (1 mmol in 6 ml of t-butyl methyl ether) was added, over a period of 12 hours, to a solution of a sulphide of formula (C) wherein R' and R" are both hydrogen (for preparation see J. Org. Chem. 44 (20) 3598–9 (1979); 198 mg, 1.0 mmol), rhodium (II) acetate (4 mg, 0.01 mmol) and benzaldehyde (190 μl, 1.0 mmol) in dichloromethane (4 ml). Upon completion of the addition, the solvent was removed in vacuo and the residue chromatographed using silica gel eluting with dichloromethane:petrol 40:60 to yield trans-2,3-diphenyl oxirane (31 mg, 16%, 51%ee) and cis-2 3-diphenyl oxirane (3 mg, 1.5%).

EXAMPLE 49

Trans-Stilbene oxide

A mixture of boron trifluoroetherate (0.01 ml; 0.77 mmol) and glacial acetic acid (0.16 ml; 2.80 mmol) in minimum chloroform (2 ml) was stirred and refluxed under nitrogen for 15 minutes. A mixture of dimethoxymethane (0.07 ml; 0.79 mmol) and (+)-(10)-mercaptoborneol (0.13 g; 0.70 mmol) in chloroform (3 ml) was then added slowly over 15 minutes. The reaction mixture was refluxed for 30 minutes, before being allowed to cool to room temperature. The reaction mixture was then washed with water (2×10 ml), brine solution (2×10 ml) and 10% aqueous potassium hydroxide (2×10 ml). The organic fraction was dried over potassium carbonate. The solvent was removed in vacuo, to yield a crude product which was chromatographed eluting with 85:15 petrol:ethyl acetate to produce a compound formula (C') wherein R' and R" are both hydrogen (91 mg; 69%). $^1$H N.M.R. data: $\delta_H$(CDCl$_3$) 4.58(1H,dd), 4.67(1H,d), 3.41–3.48(1H,m), 2.67(1H,d), 2.30–2.42(1H,m), 2.28(1H, dd), 1.91–2.13(1H,m), 1.38–1.62(2H,m), 0.96–1.22(2H,m), 0.72–0.90(1H,m), 0.74(6H,s) ppm.

A solution of phenyldiazomethane (0.45 mmol in 6 ml of t-butylmethyl ether was added to a solution of a compound of formula (C') wherein R' and R" are both hydrogen (90 mg; 0.45 mmol), rhodium (II) acetate (2 mg; 0.0045 mmol) and benzaldehyde (46 μl; 0.45 mmol) in dichloromethane (2 ml). Upon completion of the addition, the solvent was removed in vacuo and the residue chromatographed using silica gel and elating with dichloromethane:petrol 40:60 to give the title compound (4 mg, 5%, 71%ee).

EXAMPLE 50

2,3-Diphenyl-1-(4-methylphenylsulphonyl)aziridine

To a stirred solution of dimethylsulphide (7 μl, 0.1 mmol), rhodium (II) acetate (2 mg, 0.005 mmol) and N-benzylidene-toluene-p-sulphonamide (131 mg, 0.5 mmol; J. C. S. Perkin I (1981) 2435–2442) in dichloromethane (2 ml) was added phenyldiazomethane (prepared as in Example 36; 8.11 ml of a 0.074M solution in t-butylmethylether) over a period of 12 hours. Upon completion of the addition, the solvent was removed in vacuo and the residue chromatographed using silica gel eluting with 15:85 ethyl acetate:petrol to give the title compound as a 3:1 mixture of trans:cis isomers (144 mg, 82%).

EXAMPLE 51

2-(4-Nitrophenyl)-3-phenyl-1-(4-methylphenylsulphonyl)aziridine

To a stirred solution of dimethylsulphide (5 μl, 0.07 mmol), rhodium (II) acetate (2 mg, 0.005 mmol) and N-(4-nitrobenzylidene)toluene-p-sulphonamide (102 mg, 0.33 mmol; J. C. S. Perkin I (1981) 2435–2442) in dichloromethane (2 ml) was added phenyldiazomethane (prepared as in Example 36; 8.11 ml of a 0.074M solution in t-butylmethylether) over a period of 12 hours. Upon completion of the addition the solvent was removed in vacuo and the residue was chromatographed using silica gel elating with 15:85 ethyl acetate:petrol to give the title compound as a mixture of trans and cis isomers. Trans isomer (48 mg, 37%) $\delta_H$(CDCl$_3$) 8.10–8.19(2H,m), 7.53–7.64(4H,m), 6.95–7.41(7H,m), 4.27(1H,d,J=6 Hz), 4.16(1H,d,J=6 Hz), 2.36(3H,s)ppm. Cis isomer (9 mg; 7%) $\delta_H$(CDCl$_3$) 8.23–8.33(2H,m); 7.15–7.60(11H,m), 4.13(1H,d,J=2 Hz) 3.87(1H,d,J=2 Hz) 1.68(3H,s)ppm.

EXAMPLE 52

Trans-2-(4-Methoxyphenyl)-3-phenyl-1-(4-methylphenylsulphonyl)aziridine

4-Methoxybenzaldehyde (1.22 ml, 10 mmol) and p-toluenesulphonamide (1.71 g, 10 mmol) were refluxed in toluene (70 ml) for 5 minutes using a Dean and Stark apparatus. Reflux was maintained while BF$_3$(C$_2$H$_5$)$_2$O (0.05 ml, 0.4 mmol) was added via a syringe. The reaction mixture was maintained at reflux for 12 hours before being allowed to cool to room temperature whereby the title compound precipitated from the toluene. Filtration followed by recrystallisation from dichloromethane-petrol yielded N-(4-methoxybenzylidene)-toluene-p-sulphonamide as a yellow solid (0.478 g; 17%) m.p. 127° C.

To a stirred solution of dimethylsulphide (7 μl, 0.1 mmol), rhodium (II) acetate (2 mg, 0.005 mmol) and N-(4-methoxybenzylidene)toluene-p-sulphonamide (144 mg, 0.5 mmol) in dichloromethane (2 ml) was added phenyldiazomethane (prepared as in Example 36; 8.96 ml of a 0.067M solution in t-butylmethylether) over a period of 12 hours. Upon completion of the addition the solvent was removed in vacuo and the residue was chromatographed using silica gel eluting with 15:85 ethyl acetate:petrol to give the title compound (96 mg, 51%). $\delta_H$(CDCl$_3$) 7.62(2H), 6.75–7.45 (11H,m), 4.35(1H,d,J=6 Hz), 4.18(1H,d,J=6 Hz), 3.62(3H, s), 2.35(3H,s)ppm.

EXAMPLE 53

Trans-2-(N,N-Diethylacetamido)-3-phenyl-1-(4-methylphenylsulphonyl)aziridine

To a stirred solution of dimethylsulphide (0.014 ml, 0.2 mmol), rhodium (II) acetate (4 mg, 0.01 mmol) and N-benzylidenetoluene-p-sulphonamide (260 mg, 1.0 mmol) in dichloromethane (2 ml) was added a solution of N,N-diethyldiazoacetamide (prepared by using N,N-diethylacetoacetamide in place of t-butylacetoacetate in a preparation described in Org. Synth. Collective Volume V page 179; 141 mg, 1.0 mmol, in 6 ml t-butylmethyl ether) over a period of 24 hours via a syringe pump. Upon completion of the addition, the solvent was removed in vacuo to yield the title compound (56 mg; 15%). $\delta_H$(CDCl$_3$) 7.10–7.91(9H,m), 4.40(1H,d,J=4 Hz), 3.10–4.10(4H, m), 3.40(1H,d,J=4 Hz), 2.30(3H,s), 1.15(6H,m) ppm.

EXAMPLE 54

Trans-2-(N,N-Diethylacetamido)-3-(4-chlorophenyl) oxirane

To a stirred solution of tetrahydrothiophene (6 μl, 0.1 mmol), rhodium (II) acetate (2 mg, 0.005 mmol) and p-chlorobenzaldehyde (71 mg, 0.5 mmol) in dichloromethane (2 ml) was added a solution of N,N-diethyldiazoacetamide (see Example 53 for preparation, 70 mg, 0.5 mmol, in 6 ml t-butylmethyl ether) over a period of 24 hours via a syringe pump at 60° C. Upon completion of the addition, the solvent was removed in vacuo and the residue chromatographed using silica gel eluting with petrol:ethyl acetate 1:1 to yield the title compound (25 mg, 20%). $\delta_H$(CDCl$_3$) 1.14–1.30(6H,m), 3.30–3.52(4H,m), 3.53(1H,d, J=2 Hz), 4.07(1H,d,J=2 Hz), 7.22–7.40(4H,m)ppm.

EXAMPLE 55

Styrene oxide

To a solution of diethyl zinc (18 ml of 1.1M solution in toluene, 20 mmol) in 1,2-dichloroethane (60 ml) was added chloroiodomethane (2.18 ml, 30 mmol) at −15° C. and the reaction mixture was stirred for 15 minutes. Tetrahydrothiophene (2.40 ml, 30 mmol) was added at −15° C. and the mixture was stirred for 25 minutes. During this time the temperature was allowed to rise to 19° C. Benzaldehyde (2.12 ml, 20 mmol) was added and the reaction mixture was stirred until it reached room temperature. The reaction mixture was stirred at room temperature for 1 hour after which it was diluted with dichloromethane (20 ml) and washed with a saturated solution of NH$_4$Cl (3×5 ml). The organic layer was dried over MgSO$_4$. The resulting solution was analysed by gas chromatography and the title compound was found to be present.

EXAMPLE 56

2-Phenyl-3-vinyloxirane

To a stirred solution of dimethyl sulfide (1.0 mmol), rhodium (II) acetate (0.01 mmol) and acrolein (1 mmol) in dichloromethane (4 ml) was added a solution of phenyldiazomethane (1 mmol in 6 ml of tert-butyl methyl ether, prepared as in Example 1) at room temperature over a period of 3 hours. After the addition was completed the solvent was removed in vacuo and the residue was chromatographed over silica (eluant dichloromethane:petrol; 40:60) to give the title compound in 54% yield. $\delta_H$ (CDCl$_3$); 7.20(5H,m), 5.75(1H,m), 5.5(1H,dd,J=2,J=12 Hz), 4.85(1H,dd,J=2,J=12 Hz), 3.55(1H,d,J=2 Hz), 3.30(1H,dd,J=2,J=9 Hz)ppm.

EXAMPLE 57

2,3-Diphenyl-1-diphenylphosphinylaziridine

Diphenylphosphinic acid (10.0 g, 45.9 mmol) was heated gently at reflux in dry tolune (75 ml) with freshly distilled thionyl chloride (6.70 ml; 91.8 mmol) for two hours, according to the method of Jennings (Jennings, W. B; Lovely, C. J; Tetrahedron, (1991) 47 5561). The solvent was then removed in vacuo to give crude diphenyl-N-phenylmethylene phosphinic chloride (9.0 g; 83%) which was used without further purification.

P,P-diphenylphosphinic amide was prepared following the method of Jennings (ibid) by adding crude diphenyl-N-phenylmethylene phosphinic chloride (9.0 g; 38.05 mmol, prepared above) in dry dichloromethane (20 ml) to a stirred mixture of saturated ethanolic ammonia solution (100 ml) and dry dichloromethane (40 ml) cooled using an ice/salt bath. Subsequent work-up gave P,P-diphenylphosphinic amide (7.2 g; 87%).

P,P-diphenyl-N-phenylmethylene phosphinic amide was prepared following the method of Jennings (ibid) by adding titanium tetrachloride (635 ml; 5.78 mmol) in dry dichloromethane (10 ml) to a stirred solution of benzaldehyde (1.17 ml; 11.59 mmol), P,P-diphenylphosphinic amide (2.52 g; 11.59 mmol) and anhydrous triethylamine (4.84 ml; 34.78 mmol) in dry dichloromethane (50 ml) at 0° C. Upon completion of the addition, the stirring was maintained at 0° C. for a further 4 hours. Subsequent work-up gave P,P-diphenyl-N-phenylmethylene phosphinic amide (1.4 g; 40%).

To a sitrred solutuion of dimethyl sulfide (12 µl, 0.16 mmol), rhodium (II) acetate (3.5 mg; 0.0079 mmol) and P,P-diphenyl-N-phenylmethylene phosphinic amide (241 mg; 0.79 mmol) in dichloromethane (2 ml), was added a solution of phenyldiazomethane (8.4 ml of 0.094M solution in tert-butyl methyl ether), at room temperature over 14 hours via a syringe pump. Upon completion of the addition, the solvent was removed in vacuo. Chromatography using 1:1 ethyl acetate:petrol gave a mixture (6:1) of trans- and cis- 2,3-diphenyl-1-diphenylphosphinyl aziridine (205 mg, 66%). $\delta_H$(CDCl$_3$): 4.05(1.72H,d, J=16 Hz), 4.16(0.28H,d, J=18 Hz), 7.10–7.45(16H,m), 7.50–7.65(1.72H,m), 7.75–7.85(1.72H,m), 7.90–8.05(0.56H,m)ppm.

EXAMPLE 58

2-(3-Chlorophenyl)-3-phenyl oxirane

To a mixture of sodium methoxide solution (30% in methanol, 0.360 g), methanol (1.33 g) and tert-butylmethylether (5 ml) was added N-nitroso-N-(3-chlorobenzyl)-p-toluenesulphonamide (0.54 g) over 15 minutes. The resulting mixture was stirred at room temperature for 30 minutes and then refluxed for 15 minutes. Water (4 ml) was added to the mixture once it had cooled to room temperature. The organic layer was washed with further quantities of water (2×4 ml) and then dried over anhydrous sodium sulphate. After decanting the organic solution from the sodium sulphate, the sodium sulphate was washed with tert-butylmethylether (2×1 ml) and these washings were combined with the decanted organic solution of 3-chlorophenyldiazomethane.

To a slurry of rhodium (II) acetate (0.001 g) and dichloromethane (4 ml) were added benzaldehyde (0.025 ml) and dimethylsulphide (0.009 ml). The solution of 3-chlorophenyldiazomethane (produced above) was added to this mixture over 24 hours. The solvent was removed in vacuo and the residue chromatographed on silica (Merck grade 60, 230–400 mesh) eluting with dichloromethane:hexane 2:3 to give the title compound as a colourless oil (0.0305 g, 53% yield) $\delta_H$(CDCl$_3$): 7.55(8H); 7.45(1H), 4.0(2H)ppm.

EXAMPLE 59

Stilbene oxide

To a mixture of rhodium (II) acetate (0.0021 g), dichloromethane (4 ml) and benzaldehyde (0.051 ml) was added 1-methoxy-4-methylthiobenzene (0.0036 ml). To this mixture was added, with stirring, a solution of phenyldiazomethane (1 mmol in tert-butylmethyl ether (8 ml)) over 19 hours. The reaction mixture was stirred or a further 5 hours after which the mixture was allowed to stand at room temperature for 2 days. The solvent was removed in vacuo and the residue chromatographed on silica using dichloromethane:hexane 2:3 as eluant. The title compound was obtained as a colourless oil (0.0713 g, 22.6% yield).

EXAMPLE 60

2-(4-Chlorophenyl)-3-phenyloxirane

Phenyldiazomethane (1 mmol in 6 ml of tert-butyl methyl ether, as prepared in Example 1), was added to a stirred solution of dimethylsulphide (1.0 mmol), rhodium (II) trifluoroacetamide (0.01 mmol) and p-chlorobenzaldehyde (1 mmol) in dichloromethane (4 ml) at room temperature over a period of 3 hours. After the addition was completed the solvent was removed in vacuo and the residue was chromatographed over silica (eluent dichloromethane:petrol (2:3)] to give the title compound in 83% yield.

CHEMICAL FORMULAE
(AS IN DESCRIPTION)

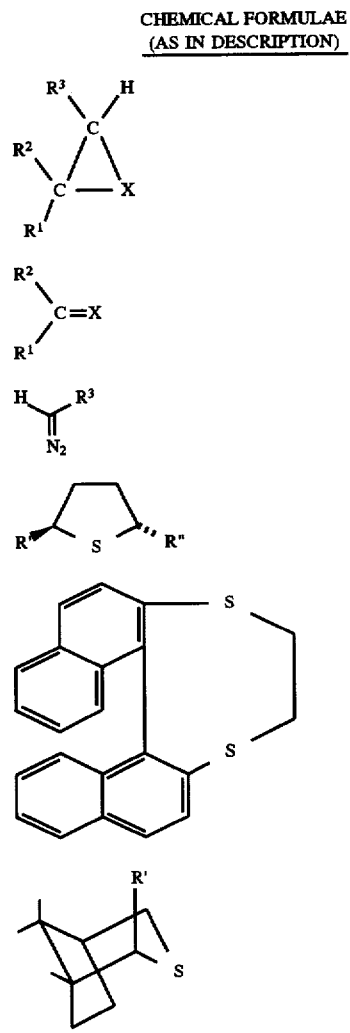

-continued
CHEMICAL FORMULAE
(AS IN DESCRIPTION)

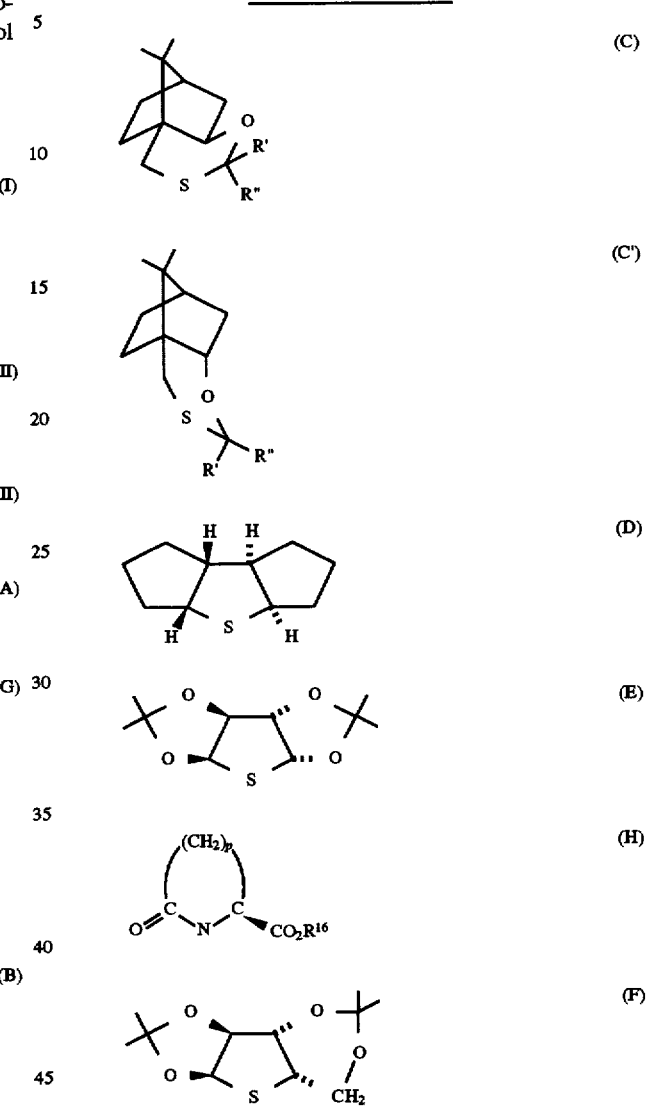

Scheme 1

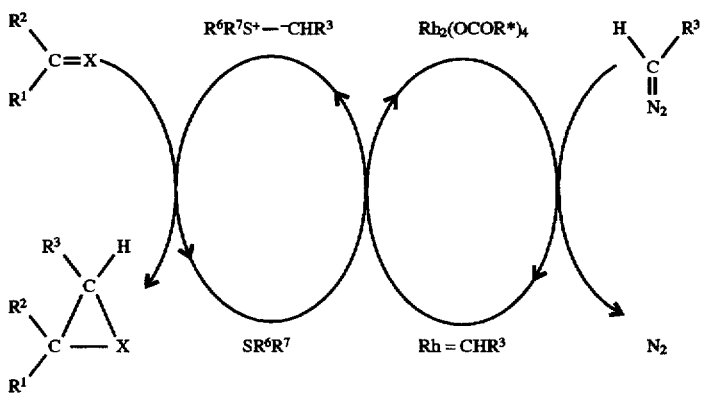

Scheme 2

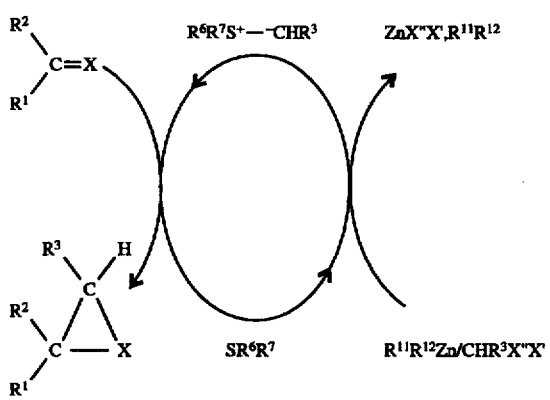

We claim:

1. A process for the preparation of an oxirane, aziridine or cyclopropane of formula (I):

wherein, X is oxygen, $NR^4$ or $CHR^5$; $R^1$ is hydrogen, alkyl, aryl, heteroaromatic, heterocyclic or cycloalkyl; $R^2$ is hydrogen, alkyl, aryl, heteroaromatic, $CO_2R^8$, $CHR^{14}NHR^{13}$, heterocyclic or cycloalkyl; or $R^1$ and $R^2$ join together to form a cycloalkyl ring; $R^3$ is hydrogen, alkyl, aryl, heteroaromatic, $CO_2R^8$, $R^8_3Sn$, $CONR^8R^9$ or trimethylsilyl; $R^4$ and $R^5$ are, independently, alkyl, cycloalkyl, aryl, heteroaromatic, $SO_2R^8$, $SO_3R^8$, $COR^8$, $CO_2R^8$, $CONR^8R^9$ or CN, or $R^4$ can also be $P(O)(aryl)_2$; $R^8$ and $R^9$ are independently alkyl, aryl or arylalkyl; $R^{13}$ and $R^{14}$ are independently hydrogen, alkyl or aryl; the process comprising:

a) reacting a metallocarbon with a sulphide of formula $SR^6R^7$, wherein $R^6$ and $R^7$ are independently alkyl, aryl or heteroaromatic, or $R^6$ and $R^7$ join together to form a cycloalkyl ring which optionally includes an additional heteroatom; and, b) reacting the product of step (a) with a compound of formula (II):

wherein $R^1$, $R^2$ and X are as defined above.

2. A process as claimed in claim 1 wherein $R^1$ is hydrogen.

3. A process as claimed in claim 1, comprising:
a) reacting an alkyl metal with a methane derivative of formula $CHR^3X'X''$;
b) reacting the product of (a) with a sulphide of formula $SR^6R^7$; and
c) reacting the product of (b) with a compound of formula (II).

4. A process as claimed in claim 1, comprising:
a) reacting a compound of formula (III) (wherein $R^3$ is not hydrogen) with a suitable organometallic or inorganic reagent;
b) reacting the product of (a) with a sulphide of formula $SR^6R^7$; and,
c) reacting the product of (b) with a compound of formula (II).

5. A process as claimed in claim 1, comprising adding a compound of formula (III) (wherein $R^3$ is as defined in claim 1 but is not hydrogen) to a mixture of a sulphide of formula $SR^6R^7$, a compound of formula (II) and an organometallic or inorganic reagent.

6. A process as claimed in claim 5 wherein the addition is over a period of 2 to 36 hours.

7. A process as claimed in claim 5 or 6 wherein the sulphide is present in a less than stoichiometric amount.

8. A process as claimed in claim 1 wherein the metallocarbon is prepared by reacting an alkylmetal with a methane derivative of formula $CHR^3X'X''$, wherein $R^3$ is as defined above, and X' and X" are independently, a leaving group.

9. A process as claimed in claim 1 wherein the metallocarbon is prepared by reacting a compound of formula (III):

wherein $R^3$ is as defined in claim 1 but is not hydrogen, with a suitable organometallic or inorganic reagent.

10. A process as claimed in claim 9 wherein the suitable organometallic or inorganic reagent is rhodium (II) acetate or copper acetylacetonate.

11. A process as claimed in claim 1 wherein the sulphide of formula $SR^6R^7$ is a compound of formula (C):

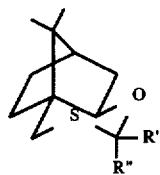

(C)

wherein R' is hydrogen, $C_{1-10}$ alkyl, phenyl or phenyl($C_{1-6}$)alkyl; wherein the alkyl groups are optionally substituted by phenyl, $C_{3-7}$ cycloalkyl, $C_{1-6}$ alkoxy, halogen, $C_{1-6}$ haloalkoxy or $CO_2(C_{1-6})$alkyl; and wherein the phenyl groups are optionally substituted by one or more of halogen, $C_{1-10}$ alkyl, $C_{1-10}$ haloalkyl, $C_{1-6}$ alkoxy, $C_{1-6}$ haloalkoxy, $C_{3-7}$ cycloalkyl, nitro, cyano or $CO_2(C_{1-6})$alkyl; and R" is hydrogen.

* * * * *